(12) United States Patent
Pratley

(10) Patent No.: US 6,569,825 B1
(45) Date of Patent: May 27, 2003

(54) AQUEOUS CLEANSING COMPOSITION COMPRISING SHORT CHAIN AND LONG CHAIN ANIONIC SURFACTANTS

(75) Inventor: Stuart Keith Pratley, West Kirby (GB)

(73) Assignee: Helene Curtis, Inc., Chicago, IL (US)

( * ) Notice: Subject to any disclaimer, the term of this patent is extended or adjusted under 35 U.S.C. 154(b) by 0 days.

(21) Appl. No.: 09/437,885

(22) Filed: Nov. 9, 1999

Related U.S. Application Data

(62) Division of application No. 08/965,519, filed on Nov. 6, 1997, now Pat. No. 6,001,787.

(30) Foreign Application Priority Data

Nov. 18, 1996 (GB) ............................................. 9623935

(51) Int. Cl.$^7$ ................................................. A61K 7/50
(52) U.S. Cl. ........................ 510/130; 510/156; 510/424; 510/426; 510/428; 510/492
(58) Field of Search .................................. 510/424, 426, 510/428, 130

(56) References Cited

U.S. PATENT DOCUMENTS

| | | | |
|---|---|---|---|
| 3,728,447 A | | 4/1973 | Osipow et al. |
| 4,761,279 A | | 8/1988 | Khalil et al. |

FOREIGN PATENT DOCUMENTS

| | | |
|---|---|---|
| EP | 0224796 | 6/1987 |
| WO | 91/09923 | 7/1991 |

*Primary Examiner*—Necholus Ogden
(74) *Attorney, Agent, or Firm*—Milton L. Honig

(57) ABSTRACT

The invention relates to an aqueous cleansing composition which comprises a combination of short and long chain anionic surfactants that provide mild cleansing and good lathering.

13 Claims, No Drawings

AQUEOUS CLEANSING COMPOSITION COMPRISING SHORT CHAIN AND LONG CHAIN ANIONIC SURFACTANTS

This is a division of application Ser. No. 08/965,519 filed Nov. 6, 1997, now U.S. Pat. No. 6,001,787.

FIELD OF THE INVENTION

The invention relates to aqueous cleansing compositions. In particular, the invention is concerned with aqueous cleansing compositions suitable for cleaning human skin and hair, which comprise a combination of certain specific long-chain and short-chain surfactants. The compositions are not only very mild but also show an excellent lather performance.

BACKGROUND TO THE INVENTION AND PRIOR ART

In the recent past it has become more and more important for consumers that aqueous cleansing compositions are high foaming as well as mild. These combined properties are especially useful if the cleansing compositions are to be topically applied to human skin and hair. Consequently, efforts have been made to provide washing products, such as hair shampoos, shower gels and facial wash foams, showing these two properties. The major problem to provide such products resides in the fact that both properties tend to be mutually incompatible. While high lathering surfactants are generally very harsh, mild surfactants tend to give insufficient lather.

In the past attempts have been made to overcome these problems by combining harsh surfactants generating sufficient lather with very mild co-surfactants.

U.S. Pat. No. 3,728,447 (C J Patterson) discloses hair shampoo compositions containing fatty acid lactylates or glycolates while the cleaning actions of these shampoos is satisfactory the foam remains minimal. In order to achieve higher foaming action it is described to incorporate booster surfactants, such as sodium lauryl sulphate or triethanol amine lauryl sulphate, in the shampoo compositions. However, these booster surfactants are causing a high degree of irritancy when applied on human skin.

WO 91/09923 describes compositions comprising an ultra mild surfactant and a foam enhancer. The ultra mild surfactant is an alkyl glyceryl ether sulfonate (AGS) which has a hydrophobic group containing a linear alkyl chain containing from about 7 to 9 carbon atoms. Conventional foam boosters such as amine oxides and water soluble halide salts are added to improve lather creaminess, volume and stability.

EP-A-224 796 (Kao) describes a detergent composition comprising (a) a phosphate surfactant and (b) an acyl lactylate having an acyl group containing 12 to 18 carbon atoms. Specific examples for such combinations are mixtures of lauryl phosphate and stearoyl lactylate, isostearoyl lactylate and lauroyl lactylate, respectively.

U.S. Pat. No. 4,761,279 (Eastman Kodak) discloses shaving cream formulations comprising salts of $C_{14}$–$C_{22}$ acyl lactylates, saturated monoglycerides, propylene glycol monoesters and humectants.

It has now been discovered that a combination of specific short-chain surfactants with specific long-chain surfactants provides mild cleansing compositions with the added attribute that by using these compositions a high degree of lather is generated. Unexpectedly, these properties have been achieved by combining very mild surfactants, which on application on their own give unsatisfactory lather in terns of foam volume. The synergistic effect obtained by combining the specific short-chain and the specific long-chain surfactant is described later herein.

DEFINITION OF THE INVENTION

Accordingly, the invention provides an aqueous cleansing composition, which comprises:

(a) a short-chain anionic surfactant chosen from $C_6$–$C_9$ alkyl ether sulphates, $C_8$–$C_{11}$ acyl lactylates, $C_6$–$C_9$ acyl methyl taurates, $C_6$–$C_9$ acyl isethionates, $C_6$–$C_{11}$ fatty acid soaps. $C_6$–$C_9$ alkyl sulphates, $C_6$–$C_{11}$ acyl sarcosinates, $C_6$–$C_9$ alkyl sulphosuccinates, $C_6$–$C_9$ alkyl ether sulphosuccinates, or mixtures thereof;

(b) a long-chain anionic surfactant chosen from $C_{13}$–$C_{18}$ alkyl ether sulphates, $C_{13}$–$C_{18}$ acyl lactylates, $C_{13}$–$C_{16}$ acyl methyl taurates, $C_{13}$–$C_{15}$ acyl isethionates, $C_{13}$–$C_{16}$ alkyl sulphates, $C_{13}$–$C_{16}$ acyl sarcosinates, $C_{13}$–$C_{16}$ alkyl sulphosuccinates, $C_{13}$–$C_{16}$ alkyl ether sulphosuccinates, or mixtures thereof;

(c) optionally, a medium-chain anionic surfactant chosen from $C_{10}$–$C_{12}$ alkyl ether sulphates, $C_{12}$ acyl lactylates, $C_{10}$–$C_{12}$ acyl methyl taurates, $C_{10}$–$C_{12}$ acyl sethionates, $C_{10}$–$C_{12}$ alkyl sulphates, $C_{12}$ acyl sarcosinates, $C_{10}$–$C_{12}$ alkyl sulphosuccinates, $C_{10}$–$C_{12}$ alkyl ether sulphosuccinates, or mixtures thereof, (d) water;

wherein (i) at least one of the surfactants (a) and (b) is selected from the group consisting of the acyl lactylates, the acyl sarcosinates, the acyl methyl taurates, the alkyl ether sulphates and the acyl isethionates; or the short-chain anionic surfactant (a) is a $C_6$–$C_{11}$ fatty acid soap;

(ii) if surfactant (c) is present, then the surfactants (a), (b) and (c) are present in an amount such that the weight ratio of (c):[(a)+(b)] is less than 1:1.

DETAILED DESCRIPTION OF THE INVENTION

Short-chain anionic surfactant (a)

The aqueous cleansing composition according to the invention comprises from 0.1 to 36% by weight of a short-chain surfactant chosen from $C_6$–$C_9$ alkyl ether sulphates, $C_8$–$C_{11}$ acyl lactylates, $C_6$–$C_9$ acyl methyl taurates, $C_6$–$C_9$ acyl isethionates, $C_6$–$C_{11}$ fatty acid soaps, $C_6$–$C_9$ alkyl sulphates, $C_6$–$C_{11}$ acyl sarcosinates, $C_6$–$C_9$ alkyl sulphosuccinates, $C_6$–$C_9$ alkyl ether sulphosuccinates, or mixtures thereof.

It is preferred to use the short-chain anionic surfactant (a) in amounts of from 0.5 to 20% preferably from 1 to 10% by weight in the cleansing composition according to the invention.

Long-chain anionic surfactant (b)

The aqueous cleansing composition according to the invention comprises from 0.1 to 36% by weight of a long-chain surfactant chosen from chosen from $C_{13}$–$C_{18}$ alkyl ether sulphates, $C_{13}$–$C_{18}$ acyl lactylates, $C_{13}$–$C_{16}$ acyl methyl taurates, $C_{13}$–$C_{15}$ acyl isethionates, $C_{13}$–$C_{16}$ alkyl sulphates, $C_{13}$–$C_{16}$ acyl sarcosinates, $C_{13}$–$C_{16}$ alkyl sulphosuccinates, $C_{13}$–$C_{16}$ alkyl ether sulphosuccinates, or mixtures thereof.

It is preferred to use the long-chain anionic surfactant (b) in amounts of from 0.5 to 20%, preferably from 1 to 10%, by weight in the cleansing composition.

Combination of short-chain surfactants (a) and long-chain surfactants (b)

The aforementioned short-chain surfactants and long-chain surfactants are combined in such a way so that at least one is chosen from the group consisting of the acyl lactylates, the acyl sarcosinates, the acyl methyl taurates, the alkyl ether sulphates, the acyl isethionates and the $C_6$–$C_{11}$ fatty acid soaps, as specified above.

This means that:

- a $C_6$–$C_9$ alkyl ether sulphate is present as short chain surfactant or a $C_{13}$–$C_{18}$ alkyl ether sulphate is present as long chain surfactant, or:
- a $C_8$–$C_{11}$ acyl lactylate is present as short-chain surfactant or a $C_{13}$–$C_{18}$ acyl lactylate is present as long-chain surfactant, or:
- a $C_6$–$C_9$ acyl methyl taurate is present as short chain surfactant or a $C_{11}$–$C_{16}$ acyl methyl taurate is present as long chain surfactant, or:
- a $C_6$–$C_9$ acyl isethionate is present as short chain surfactant or a $C_{13}$–$C_{15}$ acyl isethionate is present as long chain surfactant, or:
- a $C_6$–$C_{11}$ acyl sarcosinate is present as short chain surfactant or a $C_{13}$–$C_{16}$ acyl sarcosinate is present as long chain surfactant; or
- a $C_6$–$C_{11}$ fatty acid soap is present as short chain surfactant.

Surprisingly, it is not essential for the purposes of the invention that both types of surfactants, long and short-chain, are chosen from the same homologous series of surfactants.

The weight ratio of the short-chain surfactant (a) to the long chain surfactant (b) is preferably in the range of 1:10 to 10:1, more preferably 1:3 to 6:1 and most preferably 1:1 to 3:1.

Medium-chain anionic surfactant

The cleansing composition according to the invention optionally comprises a medium-chain anionic surfactant (c) chosen from $C_{10}$–$C_{12}$ alkyl ether sulphates, $C_{12}$ acyl lactylates, $C_{10}$–$C_{12}$ acyl methyl taurates, $C_{10}$–$C_{12}$ acyl isethionates, $C_{10}$–$C_{12}$ alkyl sulphates, $C_{12}$ acyl sarcosinates, $C_{10}$–$C_{12}$ alkyl sulphosuccinates, $C_{10}$–$C_{12}$ alkyl ether sulphosuccinates, or mixtures thereof.

Within each homologous series of surfactants, it has been found that the above mentioned medium-chain anionic surfactants (c) are the species which, of the particular series, generate the highest degree of lather according to the foam test, described herebelow. These medium-chain surfactants, on the other hand, have been found in general to be the most irritant surfactant within their respective homologous series. The medium-chain surfactant (c) exists for every homologous series of surfactants and its specific chain length or chain-length range can be determined by the foam test described herebelow.

For example, according to the foam test described below, the $C_{12}$ acyl sarcosinate, recited above as one of the medium-chain anionic surfactants (c), is the medium-chain length acyl sarcosinate. It is thus the one acyl sarcosinate generating the highest degree of lather, and is also the most irritant surfactant within the homologous series of acyl sarcosinates.

It is essential for the purposes of the present invention that the short-chain anionic surfactant (a), the long-chain anionic surfactant (b) and the medium-chain anionic surfactant (c) are present in amounts such that the weight ratio of (c):(a)+(b) is less than 1:1.

The amounts of the surfactants (a), (b) and (c) are preferably chosen so that the weight ratio of (c):(a)+(b) is less than 1:1.5 and more preferred less than 1:2. It is, however, most preferred that no medium-chain surfactant (c) is present in compositions according to the invention.

According to the teaching of the prior art high foaming compositions can only be obtained by using high foaming surfactants, in particular medium-chain surfactants, simultaneously having the disadvantage of being very skin irritant compounds. In contrast to this teaching, the present invention provides extremely mild and high lathering aqueous cleansing compositions by using very mild surfactants which when used singly do not give sufficient foam. It is surprising that by use of mild and low foaming surfactants compositions can be provided having about the same foaming properties but not the undesired skin irritancy as the medium-chain surfactant.

Water

The composition according to the invention comprises water in an amount of from 60 to 99%, preferably 96 to 70%, most preferably 92 to 78% by weight based on total weight of the composition.

Use of the composition

The invention also provides the use as a cleanser for human skin and hair of an aqueous composition which comprises:

(a) a short-chain anionic surfactant chosen from $C_6$–$C_9$ alkyl ether sulphates, $C_8$–$C_{11}$ acyl lactylates, $C_6$–$C_9$ acyl methyl taurates, $C_6$–$C_9$ acyl isethionates, $C_6$–$C_{11}$ fatty acid soaps, $C_6$–$C_9$ alkyl sulphates, $C_6$–$C_{11}$ acyl sarcosinates, $C_6$–$C_9$ alkyl sulphosuccinates, $C_6$–$C_9$ alkyl ether sulphosuccinates, or mixtures thereof;

(b) a long-chain anionic surfactant chosen from $C_{13}$–$C_{18}$ alkyl ether sulphates, $C_{13}$–$C_{18}$ acyl lactylates, $C_{13}$–$C_{16}$ acyl methyl taurates, $C_{13}$–$C_{15}$ acyl isethionates, $C_{13}$–$C_{16}$ alkyl sulphates, $C_{13}$–$C_{16}$ acyl sarcosinates, $C_{13}$–$C_{16}$ alkyl sulphosuccinates, $C_{13}$–$C_{16}$ alkyl ether sulphosuccinates, or mixtures thereof;

(c) optionally, a medium-chain anionic surfactant chosen from $C_{10}$–$C_{12}$ alkyl ether sulphates, $C_{12}$ acyl lactylates, $C_{10}$–$C_{12}$ acyl methyl taurates, $C_{10}$–$C_{12}$ acyl isethionates, $C_{10}$–$C_{12}$ alkyl sulphates, $C_{12}$ acyl sarcosinates, $C_{10}$–$C_{12}$ alkyl sulphosuccinates, $C_{10}$–$C_{12}$ alkyl ether sulphosuccinates, or mixtures thereof, and (d) water;

wherein (i) at least one of the surfactants (a) and (b) is selected from the group consisting of the acyl lactylates, the acyl sarcosinates, the acyl methyl taurates, the alkyl ether sulphates and the acyl isethionates, or the short-chain anionic surfactant (a) is a $C_6$–$C_{11}$ fatty acid soap;

(ii) if surfactant (c) is present, then the surfactants (a), (b) and (c) are present in an amount such that the weight ratio of (c):[(a)+(b)] is less than 1:1.

Compositions of the invention may be formulated for washing the hair or skin, for example, hair shampoos; rinse-off hair care products; bath or shower gels; and facial washing compositions.

Preferably the compositions according to the invention will also include a cosurfactant. The cosurfactant can be selected from any known surfactant suitable for topical application to the human body and is selected from nonionic, zwitterionic and cationic surfactants and mixtures thereof. Mild surfactants, ie. surfactants which do not damage the stratum corneum, the outer layer of skin, are particularly preferred.

Suitable nonionic surface active agents include alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxylated with an average of from 1 to 20 moles of ethylene oxide per mole of alcohol.

Preferred zwitterionic detergents are those which have an alkyl or alkenyl group of 7 to 18 carbon atoms and comply with an overall structural formula:

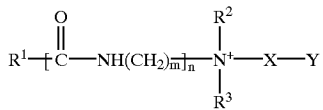

where $R^1$ is alkyl or alkenyl of 7 to 18 carbon atoms $R^2$ and $R^3$ are each independently alkyl, hydroxyalkyl or carboxyalkyl of 1 to 3 carbon atoms m is 2 to 4 n is 0 or 1

X is alkylene of 1 to 3 carbon atoms optionally substituted with hydroxyl, and

Y is —$CO_2^-$ or —$SO_3^-$

Zwitterionic detergents within the above general formula include simple betaines of formula:

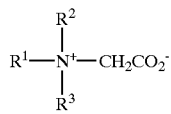

and amido betaines of formula:

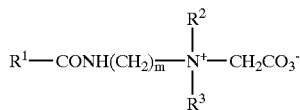

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is a sulphobetaine of formula:

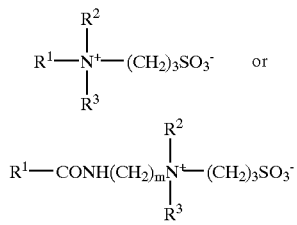

where m is 2 or 3, or variants of these in which —$(CH_2)_3SO_3^-$ is replaced by

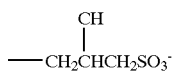

$R^1$, $R^2$ and $R^3$ in these formulae are as defined previously.

The compositions of the invention may comprise a structurant, i.e. a material added to increase the viscosity at low shear, such as less than 1 $s^{-1}$. Suitable materials include swelling clays, for example laponite; fatty acids and derivatives thereof and, in particular, fatty acid monoglyceride polyglycol ethers cross-linked polyacrylates such as Carbopol (TM) (polymers available from Goodrich); acrylates and copolymers thereof, polyvinylpyrrolidone and copolymers thereof; polyethylene imines; salts such as sodium chloride and ammonium sulphate; sucrose esters; gellants; and mixtures thereof.

Of the clays, particularly preferred are synthetic hectorite (laponite) clay used in conjunction with an electrolyte salt capable of causing the clay to thicken. Suitable electrolytes include alkali and alkaline earth salts such as halides, ammonium slats and sulphates.

The compositions according to the invention may also comprise a thickening agent, ie a material which maintains the viscosity of the composition as the shear rate thereof is increased during use. Suitable materials include cross-linked polyacrylates such as Carbopol (TM) (polymers available from Goodrich); fatty acids and derivatives particular, fatty acid monoglyceride gums including alginates, guar, derivatives including hydroxy methyl cellulose and hydroxypropyl and propylene glycol oleates; salts and ammonium sulphate; glycerol mixtures thereof.

structurants and thickeners are given in Ingredient Dictionary, Fifth by CTFA (The Cosmetic, Toiletry & incorporated herein by reference.

Examples of other adjuncts which may be added to the compositions of the invention include opacifiers; preservatives such as para-hydroxy benzoate esters; antimicrobials such as antioxidants such as butyl hydroxy toulene; bactericides; humectants such as glycerol and sorbitol; waxes; plant extracts such as Aloe Vera, witch hazel and elderflower; colourants; and perfumes.

EXAMPLES

Surfactant blends having the compositions as defined for each Example/Comparative Example were evaluated for skin mildness and lather performance according to the following protocols:

Zein test (Skin irritancy)

The skin irritancies of the various formulations was measured by the so-called Zein test. This in-vitro test method makes use of the correlation between binding ability of surfactants to proteins to the damage the surfactant causes to the skin. The de-naturation of epidermal protein structures is a key mechanism in the development of observable damage to the skin by surfactants. Zein protein, an insoluble protein extracted from corn kernel, is used as a model for epidermal protein and the solubility of the Zein protein in surfactant solutions is a reliable guide for the skin irritancy caused by the surfactant. The test involves establishing the amount of Zein protein which can be solubilised by surfactant. 5 g of Zein protein is dispersed in 40 cm3 of surfactant solution (at 2%). The mixture is shaken for 1 hour at 35 deg C., and immediately centrifuged to remove any non-solubilised Zein. The amount solubilised is estimated from the solution nitrogen content using micro-Kjeldahl method (making allowance for any nitrogen in the surfactant).

Foam volume Test

In order to assess the foaming power of the compositions, the following test was used. 25 ml of the test solution containing 10% total surfactant in distilled water, and 0.5 g of artificial sebum, are added to a 250 ml measuring cylinder. The solution is agitated by means of a rubber bung attached to a rod. The rubber bung is modified so that it has a maximum diameter 5 mm less than the internal dimensions of the cylinder. The bung is moved up and down inside the cylinder so that it passes through the solution and foam. The plunger is oscillated up and down twice per second. After 40 cycles the plunger is removed, and the volume of foam measured.

Example 1 and Comparative Examples A to C
Ether Sulphates

Comparative Example A is Linevol 79 Ether Sulphate 3EO (ex Shell) which is a blend of C7, C8 and C9 alkyl chains such that their alkyl chain length weight average is 8.2.

Comparative Example B is Dobanol 23 Ether Sulphate 3EO (ex Shell) which is a blend of C12 and C13 alkyl chains such that their alkyl chain length weight average is 12.5.

Comparative Example C is Dobanol 45 Ether Sulphate 3EO (ex Shell) which is a blend of C14 and C15 alkyl chains such that their alkyl chain length weight average is 14.5.

Example 1 is blend of Linevol 79 Ether Sulphate 3EO (ex Shell) and Dobanol 45 Ether Sulphate 3EO (ex Shell) such that their alkyl chain length weight average is 11.4.

|  | Foam volume (ml) | Zein test (% $N_2$) |
| --- | --- | --- |
| Comp.Ex A | 70 | 0.15 |
| Comp.Ex.B | 100 | 0.45 |
| Comp.Ex.C | 75 | 0.32 |
| Ex 1 | 105 | 0.22 |

Thus showing that the blend of short and long chains (Ex 1) gives equivalent lather to the intermediate chains (Comp. Ex B), but with a much lower Zein score.

Example 2 and Comparative Examples D and E
Soap and Ether Sulphate blended in the presence of Amidobetaine Comparative Example D is 10% coco Ether Sulphate (3EO) [Empicol 0251 ex Albright and Wilson]+5% coco amidobetaine [Tegobetaine C ex Goldschmidt].

Comparative Example E is 10% Sodium Caprylate soap+5% coco amidobetaine.

Example 2 is 8% Coco Ether Sulphate (3EO)+2% Sodium Caprylate soap+5% coco amidobetaine.

|  | Foam volume (ml) | Zein test (% $N_2$) |
| --- | --- | --- |
| Comp.Ex.D | 79 | 0.23 |
| Comp.Ex.E | 51 | 0.30 |
| Ex 2 | 145 | 0.24 |

Addition of the required amount of short chain soap in the blend of Example 2 has boosted lather without adversely affecting mildness (Zein) compared with a typical shampoo formulation such as is illustrated by Comparative Example D.

Example 3 and Comparative Examples F and G
Short chain Taurate and Ether sulphate blended in the presence of Amidobetaine.

Comparative Example F is 10% Coco Ether Sulphate (3EO) [Empicol 0251 ex Albright and Wilson]+5% coco amidobetaine [Tegobetaine C ex Goldschmidt].

Comparative Example G is 10% C8 Taurate+5% coco amidobetaine.

Example 3 is 7% Coco Ether Sulphate (3EO)+3% C8 Taurate+5% coco amidobetaine.

|  | Foam volume (ml) | Zein test (% $N_2$) |
| --- | --- | --- |
| Comp.Ex F | 79 | 0.23 |
| Comp.Ex G | 44 | 0.24 |
| Ex 3 | 145 | 0.24 |

Addition of the required amount of short chain Taurate in the blend of Example 3 has boosted lather without adversely affecting mildness (Zein).

Example 4 and Comparative Examples H and I
Short chain Isethionate and Ether sulphate blended in the presence of Amidobetaine Comparative Example H is 10% Coco Ether Sulphate (3EO) [Empicol 0251 ex Albright and Wilson]+5% coco amidobetaine [Tegobetaine C ex Goldschmidt].

Comparative Example I is 10% C8/10 Isethionate [containing a blend of 42% C8, 45% C10, 5% C16 5% C18]+5% coco amidobetaine.

Example 4 is 6% Coco Ether Sulphate (3EO)+4% C8/10 Isethionate+5% coco amidobetaine.

|  | Foam volume (ml) | Zein test (% $N_2$) |
| --- | --- | --- |
| Comp.Ex H | 79 | 0.23 |
| Comp.Ex I | 80 | 0.27 |
| Ex 4 | 173 | 0.25 |

Addition of the required amount of short chain Isethionate in the blend of Example 4 has boosted lather without adversely affecting mildness (Zein).

Example 5 and Comparative Examples J and K
Short chain Sarcosinate and Ether sulphate blended in the presence of Amidobetaine Comparative Example J is 10% Coco Ether Sulphate (3EO) [Empicol 0251 ex Albright and Wilson]+5% coco amidobetaine [Tegobetaine C ex Goldschmidt].

Comparative Example K is 10% C8 Sarcosinate+5% coco amidobetaine.

Example 5 is 6% Coco Ether Sulphate (3EO)+4% C8 Sarcosinate+5% coco amidobetaine.

|  | Foam volume (ml) | Zein test (% $N_2$) |
| --- | --- | --- |
| Comp.Ex J | 79 | 0.23 |
| Comp.Ex K | 42 | 0.30 |
| Ex 5 | 111 | 0.26 |

Addition of the required amount of short chain Sarcosinate in the blend of Example 5 has boosted lather without adversely affecting mildness (Zein).

Example 6 and Comparative Examples L to N
Fatty Isethionates

Comparative Example L is Coco Isethionate which is a blend of C12, C14, C16 and C18 alkyl chains such that their alkyl chain length weight average is 13.1.

Comparative Example M is C8 Isethionate.

Comparative Example N is C14 Isethionate.

Example 6 is a blend of C8 Isethionate and C14 Isethionate.

|  | Foam volume (ml) | Zein test (% N$_2$) |
| --- | --- | --- |
| Comp.Ex L | 88 | 0.42 |
| Comp.Ex M | 130 | 0.72 |
| Comp.Ex N | 0 | 0.50 |
| Ex 6 | 124 | 0.45 |

Thus showing that the blend of short and long chains (Example 6) gives equivalent lather to the medium-length chains (Comp.Ex M), but with a much lower Zein score.

Example 7 and Comparative Examples O and P

Soap and Coco Isethionate blended in the presence of Amidobetaine

Comparative Example O is 10% Coco Isethionate (average chain length C13.1)+5% coco amidobetaine [Tegobetaine C ex Goldschmidt].

Comparative Example P is 10% Sodium Caprylate soap+ 5% coco amidobetaine.

Example 7 is 7% Coco Isethionate+7% Sodium Caprylate soap+5% coco amidobetaine.

|  | Foam volume (ml) | Zein test (% N$_2$) |
| --- | --- | --- |
| Comp.Ex O | 110 | 0.23 |
| Comp.Ex P | 84 | 0.30 |
| Ex 7 | 170 | 0.30 |

Addition of the required amount of short chain soap in the blend of Example 7 has boosted lather without adversely affecting mildness (Zein).

Example 8 and Comparative Examples Q and R

Short chain Sarcosinate and Coco Isethionate blended in the presence of Amidobetaine Comparative Example Q is 10% Coco Isethionate+5% coco amidobetaine [Tegobetaine C ex Goldschmidt].

Comparative Example R is 10% C8 Sarcosinate+5% coco amidobetaine.

Example 8 is 7% Coco Isethionate+3% C8 Sarcosinate+ 5% coco amidobetaine.

|  | Foam volume (ml) | Zein test (% N$_2$) |
| --- | --- | --- |
| Comp.Ex Q | 110 | 0.23 |
| Comp.Ex R | 44 | 0.30 |
| Ex 8 | 140 | 0.27 |

Addition of the required amount of short chain Sarcosinate in the blend of Example 8 has boosted lather without adversely affecting mildness (Zein).

What is claimed is:

1. An aqueous cleansing composition, which comprises:
 (a) a short-chain anionic surfactant chosen from $C_6$–$C_9$ alkyl ether sulphates, $C_8$–$C_{11}$ acyl lactylates, $C_6$–$C_9$ acyl methyl taurates, $C_6$–$C_9$ acyl isethionates, $C_6$–$C_{11}$ fatty acid soaps, $C_6$–$C_9$ alkyl sulphates, $C_6$–$C_{11}$ acyl sarcosinates, $C_6$–$C_9$ alkyl sulphosuccinates, $C_6$–$C_9$ alkyl ether sulphosuccinates, or mixtures thereof;
 (b) a long-chain anionic surfactant chosen from $C_{13}$–$C_{18}$ alkyl ether sulphates, $C_{13}$–$C_{18}$ acyl lactylates, $C_{13}$–$C_{16}$ acyl methyl taurates, $C_{13}$–$C_{15}$ acyl isethionates, $C_{13}$–$C_{16}$ alkyl sulphates, $C_{13}$–$C_{16}$ acyl sarcosinates, $C_{13}$–$C_{16}$ alkyl sulphosuccinates, $C_{13}$–$C_{16}$ alkyl ether sulphosuccinates, or mixtures thereof;
 (c) optionally, a medium-chain anionic surfactant chosen from $C_{10}$–$C_{12}$ alkyl ether sulphates, $C_{12}$ acyl lactylates, $C_{10}$–$C_{12}$ acyl methyl taurates, $C_{10}$–$C_{12}$ acyl isethionates, $C_{10}$–$C_{12}$ alkyl sulphates, $C_{12}$ acyl sarcosinates, $C_{10}$–$C_{12}$ alkyl sulphosuccinates, $C_{10}$–$C_{12}$ alkyl ether sulphosuccinates, or mixtures thereof, and
 (d) water;
  wherein (i) at least one of the surfactants (a) and (b) is selected from the group consisting of the acyl lactylates, the acyl sarcosinates, the acyl methyl taurates, the alkyl ether sulphates and the acyl isethionates, or the short-chain anionic surfactant (a) is a $C_6$–$C_{11}$ fatty acid soap;
  (ii) if surfactant (c) is present, then the surfactants (a), (b) and (c) are present in an amount such that the weight ratio of (c):[(a)+(b)] is less than 1:1.

2. A cleansing composition according to claim 1, in which the surfactants (a), (b) and (c) are present in an amount such that the weight ratio of (c):[(a)+(b)] is less than 1:1.5.

3. A cleansing composition according to any one of claims 1, in which the surfactant (a) is selected from the group consisting of $C_8$–$C_{10}$ acyl lactylates, $C_6$–$C_8$ acyl methyl taurates, $C_6$–$C_8$ acyl isethionates, $C_6$–$C_8$ alkyl ether sulphates and $C_8$–$C_{10}$ acyl sarcosinates.

4. A cleansing composition according to claim 1, in which the surfactant (b) is selected from the group consisting of $C_{14}$–$C_{16}$ acyl lactylates, $C_{14}$–$C_{16}$ acyl methyl taurates, $C_{14}$–$C_{16}$ acyl isethionates, $C_{14}$–$C_{16}$ alkyl ether sulphates, and $C_{14}$–$C_{16}$ acyl sarcosinates.

5. A cleansing composition according to claim 1, in which the short-chain surfactant (a) and the long-chain surfactant (b) are chosen from the same homologous series of surfactants.

6. A cleansing composition according to claim 1, in which the weight ratio of surfactant (a):(b) is in the range of 1:10 to 10:1.

7. A method for cleaning human skin and hair which comprises applying a composition according to claim 1 to said human skin and hair.

8. An aqueous cleansing composition according to claim 1, wherein skin irritancy is less than or equal to 0.45% N$_2$ when measured by dispersing 5 grams of Zein protein in 40 cubic centimeters of surfactant solution at 2 wt. %, which is shaken at 1 hour at 35° C., and centrifuged to remove any non-solubilized Zein; and wherein the amount of solubilized Zein is estimated from solution nitrogen content using micro-Kjeldahl method; and wherein foam volume is 105 milliliters or more when 25 milliliters of a 10% surfactant solution is distilled water, is combined with 0.5 grams artificial sebum, placed in a 250 milliliter measuring cylinder; and agitated twice a second for 40 agitations using a rubber bung of 5 milliliters less internal dimension than the measuring cylinder, and each agitation involves passage of the rubber bung through the solution and foam, and measuring foam volume after 40 cycles of agitation.

9. A cleansing composition according to claim 1, wherein the surfactants (a), (b) and (c) are present in an amount such that the weight ratio of (c):(a)+(b) is less than 1:2.

10. A cleansing composition according to claim 1, wherein the weight ratio of surfactant (a):(b) is in the range of 1:3 to 6:1.

11. A cleansing composition according to claim 1, wherein the ratio of surfactants (a):(b) is in the range of 1:1 to 3:1.

12. A cleanser according to claim 1, wherein alkyl chain length weight average for (a), (b), and (c) is about 11.4.

13. An aqueous cleansing composition, which comprises:
(a) a short-chain anionic surfactant chosen from $C_6$–$C_9$ alkyl ether sulphates, $C_8$–$C_{11}$ acyl lactylates, $C_6$–$C_9$ acyl methyl taurates, $C_6$–$C_9$ acyl isethionates, $C_6$–$C_{11}$ fatty acid soaps, $C_6$–$C_9$ alkyl sulphates, $C_6$–$C_{11}$ acyl sarcosinates, $C_6$–$C_9$ alkyl sulphosuccinates, $C_6$–$C_9$ alkyl ether sulphosuccinates, or mixtures thereof;
(b) a long-chain anionic surfactant chosen from $C_{13}$–$C_{18}$ alkyl ether sulphates, $C_{13}$–$C_{18}$ acyl lactylates, $C_{13}$–$C_{16}$ acyl methyl taurates, $C_{13}$–$C_{15}$ acyl isethionates, $C_{13}$–$C_{16}$ alkyl sulphates, $C_{13}$–$C_{16}$ acyl sarcosinates, $C_{13}$–$C_{16}$ alkyl ether sulphosuccinates, or mixtures thereof;
(c) optionally, a medium-chain anionic surfactant chosen from $C_{10}$–$C_{12}$ alkyl ether sulphates, $C_{12}$ acyl lactylates, $C_{10}$–$C_{12}$ acyl methyl taurates, $C_{10}$–$C_{12}$ acyl isethionates, $C_{10}$–$C_{12}$ alkyl sulphates, $C_{12}$ acyl sarcosinates, $C_{10}$–$C_{12}$ alkyl sulphosuccinates, $C_{10}$–$C_{12}$ alkyl ether sulphosuccinates, or mixtures thereof, and
(d) water;
wherein at least one of the surfactants (a) and (b) is selected from the group consisting of the acyl lactylates, the acyl sarcosinates, the acyl methyl taurates, the alkyl ether sulphates and the acyl isethionates or the short chain anionic surfactant (a) is a $C_6$–$C_{11}$ fatty acid soap; and
wherein the surfactants, (a), (b) and (c) are present in an amount such that the weight ratio of (c):(a) plus (b) is less than 1:2; and the weight ratio of surfactant (a):(b) is in the range of 1:1 to 1:3; and
wherein the alkyl chain length weight average for (a), (b), and (c) is about 11.4.

* * * * *